_United States Patent_ [19]

Kvanta

[11] 4,132,597

[45] Jan. 2, 1979

[54] METHOD FOR CULTIVATION OF BACTERIA

[75] Inventor: Endre Kvanta, Angelholm, Sweden

[73] Assignee: AB Medipharm, Brogatan, Sweden

[21] Appl. No.: 694,219

[22] Filed: Jun. 9, 1976

[51] Int. Cl.$^2$ .......................... C12K 3/00; C12B 1/08; C12B 1/00

[52] U.S. Cl. .................................... 195/96; 195/108; 195/109

[58] Field of Search ................ 195/96, 104, 115, 108, 195/109, 117, 82, 120

[56] References Cited

U.S. PATENT DOCUMENTS

| | | | |
|---|---|---|---|
| 3,308,035 | 3/1967 | Douros | 195/96 X |
| 3,342,695 | 9/1967 | Felsenfeld | 195/115 |
| 3,419,473 | 12/1968 | Dawson | 195/104 |
| 3,504,185 | 3/1970 | Zweig et al. | 195/103.5 R X |
| 3,865,691 | 2/1975 | Ridway et al. | 195/82 |
| 3,898,959 | 8/1975 | Chen et al. | 195/115 |

OTHER PUBLICATIONS

Contois, D., "Kinetics of Bacterial Growth: Relationship Between Population Density and Specific Growth Rate of Continuous Cultures", _J. Gen. Microbiol._, vol. 21, (1959), pp. 40–50.

_Primary Examiner_—Thomas G. Wiseman
_Attorney, Agent, or Firm_—Lerner, David, Littenberg & Samuel

[57] ABSTRACT

A method for cultivating fast growing bacteria and their stable metabolites in order to reach optimal cultivating time is disclosed which comprises introducing a volume of inoculum containing the bacterium sought to be cultivated and a quantity of nutriment containing a nitrogen source, growing factors, a carbon source, and a pH-stabilizer into a fermentor. The volume of inoculum in the fermentor is utilized as a production determinative factor and is determined according to the following equation:

$$a = V \cdot n / 2^t$$

where
$a$ = volume of inoculum in liters
$V$ = cultivating medium's total volume in liters
$n$ = bacterium strain's generation time in hours
$t$ = cultivating time in hours.

The result is that a grown cultivating medium is obtained which includes a mass of the desired bacterium.

4 Claims, No Drawings

METHOD FOR CULTIVATION OF BACTERIA

BACKGROUND OF THE INVENTION

At present, there are two known methods for cultivating bacteria and their metabolites. These methods are generally described as batch and continuous cultivating.

A suitable liquid medium for cultivation should contain a nitrogen source (pepton or trypton), necessary growing factors (autolized yeast or yeast extract), and a carbon source, suitably glucose or lactose. If desired, a suitable base can be used as a pH-stabilizer. Generally, all such solutions should be autoclaved in accordance with the substratum manufacturer's instructions. However, if ammonia is used as a base, this should first be sterile filtrated.

A specific cultivating medium may, for example, have the following composition: 10 g trypton or pepton (Oxoide or Difco); 3 g yeast extract (Oxoide or Difco); 20 g glucose or lactose, purum or puriss (the quantities are stated per liter of cultivating medium). Generally, pH-adjustment can be made with 0.5 M NaOH or $NH_3$ to 6.2–7.0, and preferably to 6.5. Typical temperatures for cultivating are from about 28° to 35° C, and preferably 31° C.

Cultivation according to the prior art techniques was accomplished in the case of a strain of Streptococcus faecium, specifically S.faecium M74 utilizing the aforementioned cultivating medium and by means of adjusting units (pH and temperature) in a 10 liter BIOTEC-fermentor. The strain S.faecium M74 is deposited at the National Collection of Industrial Bacteria, Torry Research Station, Aberdeen, Scotland, with the number NCIB 1181 and has been given the code name S.faecium M74. Generation time for S.faecium M74 is approximately 20 minutes under the above-mentioned conditions. Under such conditions, a fully grown medium will contain approximately $10^{10}$ V.C./ml S.faecium M74 organisms after 5 hours. One hundred milliliters of a 12-hour-culture of S.faecium M74 in the same medium as above, but without pH-adjustment, yields a cell quantity of approximately $10^8$ V.C./ml.

As noted above, this cultivating method can be applied to batch cultivating as well as continuous cultivating. When cultivating the investigated S.faecium M74 strain continuously, it was found that the maximum diluting rate was 0.5/h under the above-mentioned conditions. Large-scaled tests confirmed, however, that yet a third cultivating method was to be preferred. This cultivating method, which is known as pulsatory cultivation, is the subject of the present invention.

DETAILED DESCRIPTION

Cultivation according to the present invention is made in a conventional cultivating jar, for example, utilizing the above-mentioned BIOTEC-fermentor in the ordinary way. It has been found that by introducing a volume of inoculum including the bacterium sought to be cultivated and a quantity of conventional nutriment containing a nitrogen source, growing factors, a carbon source, and a pH-stabilizer into the fermentor, a grown cultivating medium is obtained which includes a mass of the desired bacterium. Specifically, the volume of inoculum introduced is utilized as a production determinative factor and estimation of pulse time and volume of inoculum, can be made by means of the following formula:

$$a = V \cdot n / 2^t$$

where
a = volume of inoculum in liters
V = cultivating medium's total volume in liters
n = bacterium strain's generation time in hours
t = cultivating time in hours.

The preferred method of introducing the inoculum is to begin cultivation in a conventional manner as described above and when the stationary phase of growth has entered, the grown cultivating medium is poured off for separation or by centrifugation. The fermentor is then emptied except for a certain volume of cultivating medium which is left in the fermentor which corresponds to the desired volume of inoculum. New medium is then poured into the fermentor and the growth begun. The exponential growing phase then starts immediately without any lag phase. The pulse time, i.e. the time between tappings (cultivating time plus tapping time) is determined by the remaining cultivation medium volume, i.e., the volume of inoculum. A specific example of pulsatory cultivation of S.faecium M74 according to the present invention is as follows:

A cultivating time of 6 hours and a total volume of fully grown medium of 10 liters (including approximately 0.5 liters of 0.5 M $NH_3$ used as a pH-adjustment medium) are chosen. As noted above, the generation time of S.faecium M74 is 20 minutes or 0.33 hours. Tapping is to be done at 1 to 2 hours after the stationary phase has entered as the bacteria will be of dyplococc form at tapping. Thus, tapping will occur at 7 hours at the earliest, and 8 hours at the latest after start; that is, after the nutriment is added to the inoculum.

The volume of inoculum a shall be:

$$a = 10 \cdot 0.33 / 2^6 = 0.05 \text{ liters (approximately 50 ml)}.$$

After growth is completed, bacterium mass is separated from the cultivating medium by means of a continuous centrifuge such as, for example, EMS or Sorwall refrigerating centrifuge. Alternatively, any suitable separator which parts the medium into two liquid fractions, one of which contains the bacterium mass, can be used. The centrifugation method is preferable to the other ones, however, since it can be accomplished at low temperature and since the sediment will contain considerably less fragments from the cultivating medium which may contain unwanted metabolites than the bacterium phase at separation. If desired, the bacterium mass can be mixed with additives and freeze-dried in the conventional way.

The process of the present invention exhibits a number of practical advantages when compared with both the batch cultivation and continuous cultivation methods of the prior art. Compared to batch cultivation, pulsatory cultivation has the following advantages: it is quite flexible as regards production volume and equipment; it exhibits fewer risks as regards genetic changes; the requirement of service (cleaning and starting) is less than in the case of batch cultivation owing to the fact that cultivating can go on for a long period of time without any interruption; and the construction's production capacity can be varied within a wide interval and can be adopted to different demand by changing the volume of inoculum in accordance with the method described above.

The advantages of the pulsatory cultivation method of the present invention when compared with continuous cultivation are: flexibility as regards the production capacity and running conditions; easier procedure when collecting the bacterium sediment by batch separation or by centrifugation; and, specifically in the case of bacterium S.faecium M74, the advantage that such bacterium appears in the form of dyplococc after pulsatory cultivation, by mainly in the form of chains with irregular length after continuous cultivation. In regard to this last advantage, this is of considerable importance as a standardization of bacteria preparations containing streptococci or lactobacilli considering the quantity of living organisms per unit, which prescribes that the bacteria mainly appear in a certain shape. When counting directly on agar plates, the colonies are counted and each colony corresponds to a bacterium, no matter how many cultivated at inoculation of a possible chain, that has grown to a colony. The chain formation of the examined streptococci may be the probable reason why the culture medium at continuous cultivation always contained less living cells according to results from direct counting than the medium at pulsatory cultivation.

While the invention has been disclosed with a certain degree of particularity, it is to be understood that the present disclosure has been made by way of example only and that numerous variations, apparent to those skilled in the art, may be made without departing from the spirit and scope of the invention as hereinafter claimed.

What is claimed:

1. A method for cultivating fast growing bacteria and their stable metabolies in order to reach optimal cultivating time comprising:

choosing a volume of inoculum including the bacteria sought to be cultivated according to the following equation:

$$a = V \cdot n/2^t$$

where
- $a$ = volume of inoculum in liters
- $V$ = cultivating medium's total volume in liters
- $n$ = bacterium strain's generation time in hours
- $t$ = cultivating time in hours;

introducing said volume of inoculum and a quantity of nutriment containing a nitrogen source, growing factors, a carbon source, and a pH-stabilizer, into a fermentor therby obtaining the total volume of cultivating medium V; cultivating said bacteria by maintaining said inoculum and said nutriment in contact within said fermentor for a time t whereby a grown cultivating medium is obtained which includes a mass of the desired bacterium, wherein said volume of inoculum is introduced into said fermentor by causing bacteria to grow in said fermentor in the presence of a quantity of nutriment containing a nitrogen source, growing factors, a carbon source, and a pH-stablizer, and pouring off grown cultivating medium when the exponential growing phase has finished and the stationary phase of growth has begun, the quantity of medium poured off being such that the desired volume of inoculum remains.

2. The method of claim 1 wherein said bacterium mass is separated from said cultivating medium.

3. The method of claim 2 wherein said separation comprises centrifugation.

4. The method of claim 2 wherein said bacterium mass after separation from said medium is mixed with additives and freeze-dried.